United States Patent [19]

Schram et al.

[11] 3,944,627

[45] Mar. 16, 1976

[54] HYDROGENOLYSIS OF PHENYL ALKYL KETONES AND 1-PHENYLALKANOLS

[75] Inventors: Cornelis W. A. Schram; Freddy Wattimena, both of Amsterdam, Netherlands

[73] Assignee: Shell Oil Company, Houston, Tex.

[22] Filed: May 23, 1974

[21] Appl. No.: 472,764

[30] Foreign Application Priority Data

May 23, 1973 Netherlands.................... 7307174

[52] U.S. Cl.............................................. 260/668 R
[51] Int. Cl.².......................................... C07C 15/04
[58] Field of Search................. 260/668 R, 669 QZ

[56] References Cited

UNITED STATES PATENTS 3,424,806  1/1969  Golden et al................ 260/669 QZ

*Primary Examiner*—Delbert E. Gantz
*Assistant Examiner*—G. J. Crasanakis

[57] ABSTRACT

A process is disclosed for the production of alkylbenzenes by contacting phenyl alkyl ketones and/or 1-phenylalkanols with hydrogen in the presence of a supported noble metal of Group VIII at a temperature above about 175°C.

8 Claims, No Drawings

HYDROGENOLYSIS OF PHENYL ALKYL KETONES AND 1-PHENYLALKANOLS

BACKGROUND OF THE INVENTION

1. Field of the Invention

This invention relates to a process for the production of alkyl benzene by hydrogenolysis of phenyl alkyl ketones and/or phenyl alkanols in which alkanols the alkanol moiety has at least two carbon atoms and the phenyl and hydroxyl groups are attached to the same carbon atom. These phenyl alkanols are hereinafter referred to as "starting alcohols".

2. The Prior Art

In certain processes for the epoxidation of ethylenically unsaturated compounds utilizing alpha-alkylphenyl hydroperoxides, 1-phenylalkanols and phenyl alkyl ketones are co-produced. Reconversion of these latter two compounds back to the hydroperoxide by hydrogenolyzing them back to alkylbenzene and oxidizing the alkylbenzene to the hydroperoxide improves the economics of the process by a recycling the by-products of the epoxidation reaction. Epoxy compounds are important intermediates for chemical manufacture and are also valuable and important materials of commerce.

Straus et al. in *Ann.*, 439 (1924) at pages 298 and 299 demonstrates the production of ethylbenzene by passing hydrogen at atmospheric pressure at a temperature of 13°C through a solution of methyl phenyl ketone in acetone containing finely divided palladium. Ethylbenzene is produced in a yield of 95%, but this method of hydrogenalysis took more than 11 hours. Golden et al. in U.S. Pat. No. 3,424,806 shows that the starting alcohols in the liquid phase in the presence of one or more metals of the platinum groups as catalyst at a temperature of at least 50°C are hydrogenalyzed to the corresponding alkyl-aromatic hydrocarbons. He also states, however, that at temperatures above 120°C hydrogenation of the aromatic ring takes place with consequent loss in yield of hydrogenolysis product.

Hata et al in *Bull. Chem. Soc. Japan*, 31 (1958), at pages 773 to 776 discloses the hydrogenolysis of methyl phenyl ketone at 203°C to ethylbenzene in the vapor phase, using a nickel catalyst.

Khoobiar in British Pat. No. 1,116,378 discloses the hydrogenolysis of an aryl carbinol obtained in an oxidation process at 150°–500°C to the corresponding alkyl-aromatic hydrocarbon in the presence of a specific, but non-group VIII noble metal catalyst. Huneck in *Naturwissenschaften*, 48 (1961) at page 73 shows the hydrogenolysis of methyl phenyl ketone to ethyl benzene at 180°C to 200°C in the presence of a Cu-Cr catalyst.

Kindler et al., in *Ann.*, 605 (1957) at pages 200 to 211 demonstrates the hydrogenolysis of methyl phenyl ketone and 1-phenylethanol to ethylbenzene In the presence of colloidal al. or platinum at ambient temperature.

SUMMARY OF THE INVENTION

In accordance with the present invention, it has been found that alkylbenzenes can be prepared at rapid rates and high yields by contacting phenyl alkyl ketones and/or 1-phenylalkanols wherein the alkanol moiety has at least two carbon atoms with hydrogen in the presence of a supported noble metal of Group VIII at a temperature above about 175°C.

DETAILD DESCRIPTION OF THE INVENTION

The invention can be described as relating to a process for the preparation of alkylbenzenes by hydrogenolysis of phenyl alkyl ketones and/or phenyl alkanols in which alkanols the alkanol moiety has at least two carbon atoms and which have the phenyl and the hydroxyl groups attached to the same carbon atom by contacting these materials with supported noble metal catalyst(s) of Group VIII of the Periodic Table of the Elements (as defined in the *Handbook of Chemistry and Physics*, 40th Edition, Chemical Rubber Publishing Company at page 446).

Reference to "noble metals of Group VIII or "noble metals" includes ruthenium, rhodium, palladium, osmium, iridium and platinum. Mixtures of noble metals are also utilized, for example, platinum with palladium or platinum with rhodium.

The catalyst is supported on a variety of carriers, for example on aluminum oxide, silicon oxide, magnesium oxide, pumice, magnesium carbonate, carbon, barium sulphate or asbestos or a mixture of two or more of these carriers, for example of aluminum oxide and silicon oxide or of aluminum oxide and magnesium oxide. Porous oxidic carriers are to be preferred. More suitable carriers are particularly aluminum oxide and silicon oxide or physical mixtures of these oxides. Aluminum oxide, also called alumina, is preferred, especially because the noble metal can very suitably be supported on it with a high degree of dispersion and the metal remains well dispersed even during use of the catalyst. Examples of aluminum oxides which are utilized are alpha, gamma, eta and theta-aluminum oxide. Commercially available aluminas produced according to methods conventional in the art, for example by precipitation from an aluminum salt solution or from an aluminate solution, are useful supports. Many commercial aluminum oxides contain small amounts of contaminants, for example halogen or sulphate. It is preferred to apply a carrier which is free or almost free from sulphate, as the use of sulphate containing carriers especially at temperatures above 350°C, results in the formation of sulphur-containing reaction products.

The specific surface of the carrier has no critical limits. It has been found that conversion rises with an increasing specific surface. In view of this it is preferred to use carriers with a specific surface between about 10 m$^2$/g and about 300 m$^2$/g. The specific surface can be determined by means of the BET method as explained by Paul H. Emmett chapter 2 of the book "Catalysis", part I (Reinhold Publishing Corporation).

The amount of the noble metal applied in relation to the carrier, is varied within wide limits. Weight percentages of the noble metal (based on the carrier) of from about 0.01% to about 1.5% are very suitable; percentages between about 0.3% and about 1% are preferred, especially when utilized for the conversion of phenyl alkyl ketones where very high conversions are reached using metal concentrations above about 0.3%. On the other hand, when the starting alcohols are used, very high rates of conversions can be obtained at metal concentrations below about 0.3%. There is no inherent upper limit to the amount of metal catalyst useful, this limit being determined primarily by economic considerations.

The supported catalyst is used in particles of shapes of any form desired, for example, in the form of powsers, flakes, pills, cylinders, bars or rings. The noble metal is provided on the catalyst support in all kinds of ways, for example, only on the outside of the particles or in an outer skin of the particles or is distributed in the particles more or less homogeneously. The physical dimensions of the particles are not limited either; the largest size of a particle may, for example, be between 0.05 and 15 mm. It has been found that the size of the particles has little or no influence on the conversion and on the selectivity for alkyl benzene.

The noble metals are supported on the carrier in various ways, for example, by impregnating the carrier with a solution in water of hexachloroplatinic acid ($H_2PtCl_6$), or tetraammineplatinum hydroxide (($Pt(NH_3)4(OH)_2$ or of rhodium nitrate ($Rh(NO_3)_3$). Various degrees of dispersion of the precious metals on the carrier are applied. The compounds of the precious metals are converted into the metal itself in any suitable way, for example, by heating in air a temperature between, for example, about 450°C and about 550°C followed by reduction, for example with hydrogen, or with carbon monoxide of the oxide formed in this heating, at a temperature of at least about 150°C, for example between about 225°C and about 400°C. In many cases it is sufficient for the present hydrogenolysis to heat the carrier containing a compound of a noble metal, for example a platinum, palladium or rhodium compound in a hydrogen containing atmosphere, before the compounds to be hydrogenolysed are contacted with the catalyst.

Although there exists no critical upper limit, the alkyl moiety of the phenyl alkyl ketones used in this invention will have at least one carbon atom and up to about twenty carbon atoms, preferable from one to about ten carbon atoms and more preferable from one to about four carbon atoms, and the alkanol moiety of the phenyl alkanols used in the invention will have at least two carbon atoms and up to about twenty carbon atoms, preferable from two to about ten and more preferable from two to about four carbon atoms. The phenyl group may optionally be substituted with alkyl groups. When reference is made herein to "phenyl alkyl ketones and/or phenyl alkanols", the reference is to either phenyl alkyl ketones, or phenyl alkanols, or a mixture of phenyl alkyl ketones with phenyl alkanols.

Examples of phenyl alkyl ketones and starting alcohols which can be useful according to the present invention are methyl phenyl ketone, ethyl phenyl ketone, propyl phenyl ketone, isopropyl phenyl ketone, methyl-4-methyl phenyl ketone, 1-phenyl ethanol, 1-phenyl propanol, 1-phenyl-2-methyl propanol, 2-phenyl-2-propanol, 1-(4-methyl phenyl) ethanol, 1-phenyl-2-methyl propanol and 2-(4-isopropyl phenyl)-2-propanol. Very good results have been obtained with methyl phenyl ketone and 1-phenylethanol.

The process of the invention is carried out either continuously or batchwise. In the case of continuous operation a liquid or preferably a gaseous starting mixture containing the phenyl alkyl ketones and/or starting alcohols, is passed with hydrogen through a fixed or fluidised bed of the catalyst. It has been found that when applying high space velocities the phenyl alkyl ketones and the starting alcohols are still converted in a very high degree. When applying space velocities exceeding 60 liters per kilogram of catalyst per hour (1/kg/hour) conversions of more than 90% are recorded, whereas at space velocities of up to 200 1/kg/hour the conversion is still satisfactory. With space velocities falling below about 10 1/kg/hour and especially below about 2 1/kg/hour conversion approaches about 100%. Therefore it is preferred in most cases to adjust the space velocity at a rate between about 2 1/kg/hour and about 200 1/kg/hour most preferably between about 10 1/kg/hour and about 60 1/kg/hour; however space velocities below 2 1/kg/hour and above 200 1/kg/hour are by no means excluded.

The reaction mixture formed contains the alkylbenzene product, alkylcyclo hexane derived from this alkylbenzene, water, hydrogen, and it also contains small amounts of starting alcohol, the cyclohexyl alcohol derived from the starting alcohol and the alkyl cyclo hexyl ketone derived from the alkyl phenyl ketone. It is found that at temperatures above about 175°C and especially above 250°C the rate of reaction and the selectivity to alkylbenzene increases sharply. By the selectivity to a certain compound is meant the molar percentage this particular compound forms of the total compounds produced from the phenyl alkyl ketones and the starting alcohols. At temperatures rising above 175°C the selectivities to alkylcyclohexane and alkyl cyclohexyl ketone increase, but they sharply decrease at temperatures rising above approximately 200° or 250°C. At temperatures rising above 175°C cyclohexyl alcohols are formed to a small extent and at temperatures rising above 200°C they are not formed or formed only in small quantities. At temperatures above 250°C selectivities to alkylbenzene above 99% can be reached. In view of the above, the temperature is preferably maintained at value between about 250°C and about 375°C. However, temperatures above 375°C may be used, say up to about 450°C or higher.

In order to obtain a maximum conversion it is preferred to apply the hydrogen in a molar ratio of hydrogen: (phenyl alkyl ketone + starting alcohol) which is higher than the stoichiometric ratio. The stoichiometric molar ratios of hydrogen:alkyl phenyl ketone and hydrogen:starting alcohol are 2 and 1 respectively. The pressure is not critical and is usually between about 2 bars and 40 bars absolute. Pressures lower than 2 and higher than 40 bars are permissible.

When a freshly prepared or freshly regenerated amount of catalyst is utilized, the starting alcohols are wholly or almost wholly converted into alkylbenzenes, but the phenyl alkyl ketones are usually converted in a continuously decreasing degree after an initially complete or substantially complete conversion. This drop in the conversion of phenyl alkyl ketones proceeds, however, relatively slowly when more than 0.3% by weight of the noble metal, based on the carrier, is applied. The rate of this decrease can be reduced further by (a) increasing the pressure by raising the partial pressure of the hydrogen, and/or (b) increasing the molar ratio of hydrogen: (phenyl alkyl ketone + starting alcohol) and/or (c) decreasing the temperature. When the temperature drops below 325°C it is often observed that after an initial decrease, the conversion of the phenyl alkyl ketone reaches a constant rate while maintaining a high selectivity for alkyl benzene.

The content of alkylcyclohexane in the reaction product rises with an increasing hydrogen partial pressure and a falling temperature. It is observed, however, that the hydrogenation of alkylbenzene to alkylcyclohexane usually proceeds so slowly that the thermodynamic equilibrium is not reached. When applying the relatively high space velocities that the present invention permits, however, it appears that the alkylcyclohexane content in the reaction product is usually considerably lower than would be the case if thermodynamic equilibrium condition were obtained under the prevailing conditions. This low ethylcyclohexane content is, of course, an important advantage.

It is desirable to use conventional techniques to prevent the temperature of the reaction mixture from rising too high. The heat developed is, for example, discharged by means of indirect heat exchange, or, preferably is absorbed by a diluting agent present in the reaction mixture. It is possible to apply so much diluting agent that a substantially adiabatic execution of the hydrogenolysis is feasible. In this case of execution in the gas phase, inert diluting agents, for example nitrogen, a noble gas or an alkane can be used under the reaction conditions. It is preferred to apply the alkylbenzene to be prepared as the diluting agent. This alkylbenzene is not inert, for a small part will be hydrogenated into the alkylcyclohexane derived from it. From the following description it appears that this is not a drawback. From the reaction product formed in the hydrogenolysis, alkylbenzene and the alkylcyclohexane derived from it can be separated after condensation and separation of hydrogen and water by means of fractional distillation. The alkylcyclohexane separated can be recycled to the phenyl alkyl ketones and starting alcohols to be hydrogenolysed, as a result of which little or no alkylbenzene will be hydrogenated into alkylcyclohexane during the hydrogenolysis. When the hydrogen partial pressure is increased more alkylcyclohexane if formed, but this hydrogenation is counteracted when at the same time the content of alkylcyclohexane in the starting mixture is increased. As the application of relatively high hydrogen partial pressures, to be achieved by adjusting the total pressure to, for example, 25–35 bars absolute, makes it possible for the catalyst to be used for a very long period at a stretch, it is preferred to isolate the alkylcyclohexane from the reaction mixture and to recycle it wholly or partly to the phenyl alkyl ketones and/or phenyl alcohols to be hydrogenolysed.

After the activity of the catalyst has fallen to an unacceptably low level, the catalyst is, if desired, regenerated by burning the carbonaceous material present on the surface with an oxidizing gas. The oxidizing gas applied may be, for example, air, air enriched with oxygen or air that has been diluted with an inert gas, for example, nitrogen. The regeneration is executed at a temperature between for example about 300°C and 450°C.

The present invention is of importance for the catalytic epoxidation of ethylenically unsaturated compounds by means of an aromatic hydroperoxide of which the hydroperoxy and the phenyl group are attached to the same carbon atom. The reaction mixture formed in the epoxidation generally contains epoxide, non-converted ethylenically unsaturated compound, epoxidation catalyst in case it is homogeneous, phenyl alkyl ketone, starting alcohol, alkylbenzene, compounds with a boiling point lower and compounds with a boiling point higher than that of the six compounds mentioned. The phenyl alkyl ketone, the starting alcohol and the alkylbenzene are usually easily isolated collectively, by means of distillation. If desired, this can be done together with the compounds having a higher boiling point than that of the six compounds mentioned. This isolated mixture is combined with the reaction mixture obtained according to the present invention — after hydrogen, water and alkylcyclohexane have been separated from this reaction mixture — and from the combined mixtures alkylbenzene is isolated by means of fractional distillation. The compounds having a boiling point higher than that of the five compounds mentioned, optionally including the epoxidation catalyst, are removed and a fraction is obtained containing phenyl alkyl ketone, starting alcohol and alkylbenzene. The latter fraction can be hydrogenolysed according to the present invention, optionally together with the recycled reaction mixture from which hydrogen and water have been separated. The alkylbenzene isolated is converted in a well-known manner back to the hydroperoxide derived from it, which, if desired, can be recycled in the catalytic epoxidation. Examples of catalytic epoxidations are those of alkyl chloride into epichlorohydrin and of propene into propene oxide by means ethylbenzene hydroperoxide.

The invention is further illustrated with reference to the following illustrative embodiments which are provided for illustration and are not to be construed as limitiing the invention. The space velocities have been indicated in liter (phenyl alkyl ketone plus starting alcohol)/kg catalyst/hour.

ILLUSTRATIVE EMBODIMENT I

A commercial material which consisted of aluminum oxide containing 0.8% by weight of platinum, 0.81% by weight of sulphate, calculated as sulphur and 0.76% by weight of chloride calculated as chlorine, was tested as a catalyst. The aluminum oxide had a specific surface of 234 m$^2$/g and a pore volume of 0.64 ml/g. The catalyst was present in particles with maximum measurements between 0.177 and 0.420 mm and had a bulk density of 0.57 g/ml. The catalyst was tested in a tube used as a fixed bed with a diameter of 2 cm and a height of 8 cm. With this bed 8 experiments were carried out. With each experiment methyl phenyl ketone diluted with 4 parts by weight of n-decane was passed through the bed in a downward direction together with hydrogen. The temperature, pressure and molar ratio of hydrogen: methyl phenyl ketone were varied as indicated in Table A. The methyl phenyl ketone was passed through the bed with a low space velocity — 0.9 l/kg/hour — because in the experiments 1 and 2, which are not according to the invention, the hdyrogenolysis takes a relatively long time. Table A also shows the conversion obtained of methyl phenyl ketone as well as the selectivities to five compounds and to compounds with an atmospheric boiling point below 125°C. The total time of the experiments was 50 hours.

Table A

| Exp. No. | Temp. °C | pressure bars | mol. ratio H$_2$: methyl phenyl ketone | conversion % | selectivity to...mol.% | | | | | compounds with a boiling pt. below 125°C |
|---|---|---|---|---|---|---|---|---|---|---|
| | | | | | ethyl-benzene | ethyl-cyclohexane | 1-phenyl ethanol | 1-cyclohexyl ethanol | methyl cyclohexyl ketone | |
| 1 | 120 | 10 | 4 | 98.4 | 5.0 | 18.5 | 1.0 | 73.4 | 2.1 | 0 |
| 2 | 140 | 10 | 4 | 97.6 | 9.3 | 25.8 | 1.1 | 61.3 | 0.8 | 0 |
| 3 | 200 | 10 | 4 | 100 | 36.6 | 51.0 | 0.8 | 1.4 | 10.6 | 0 |

Table A-continued

| Exp. No. | Temp. °C | pressure bars | mol. ratio H$_2$: methyl phenyl ketone | conversion % | selectivity to...mol.% | | | | methyl cyclohexyl ketone | compounds with a boiling pt. below 125°C |
|---|---|---|---|---|---|---|---|---|---|---|
| | | | | | ethyl-benzene | ethyl-cyclohexane | 1-phenyl ethanol | 1-cyclohexyl ethanol | | |
| 4 | 200 | 10 | 2.5 | 86.4 | 63.7 | 22.7 | 0 | 0.2 | 13.4 | 0 |
| 5 | 300 | 10 | 2.5 | 100 | 99.3 | 0.4 | 0 | 0 | 0 | 0.2 |
| 6 | 300 | 20 | 2.5 | 100 | 72.5 | 27.4 | 0 | 0 | 0 | 0.1 |
| 7 | 300 | 5 | 2.5 | 100 | 99.5 | 0.1 | 0 | 0 | 0 | 0.4 |
| 8 | 300 | 5 | 4 | 100 | 98.8 | 0.9 | 0 | 0 | 0 | 0.3 |

ILLUSTRATIVE EMBODIMENT II

After the experiments described in Illustrative Embodiment I had been finished, a mixture containing 60% by weight of ethylbenzene, 33.5% by weight of 1-phenylethanol and 6.5% by weight of methyl phenyl ketone was passed through the bed together with hydrogen at a space velocity of 1.8 1/kg/hour. The pressure was 5 Bar abs. and the molar ratio of hydrogen: (methyl phenyl ketone + 1-phenylethanol) was 1.45. The conversion and the composition of the reaction product was determined after 31 and 51 hours of operation at a temperature of 300°C. After 51 hours of operation, the temperature was raised to 350°C and conversion and composition of the reaction product were determined 2 hours later. The results are shown in Table B.

Table B

| Temp. °C | hours of operation | conversion (1-phenyl-ethanol + methyl phenyl ketone)% | composition reaction product, mol% | | |
|---|---|---|---|---|---|
| | | | ethyl-benzene | ethyl-cyclohexane | styrene |
| 300 | 31 | 100 | >99 | <1 | 0 |
| 300 | 51 | 95.5 | 98 | <1 | <1 |
| 350 | 53 | 97.5 | 98 | <1 | <1 |

The starting mixture and the reaction mixtures obtained were free from sulphur. Raising the temperature to 400°C, after 53 hours of operation, resulted in the reaction product containing sulphur compounds.

ILLUSTRATIVE EMBODIMENT III

Preparation of catalyst A

A very pure commerical aluminum oxide was heated for 1 hour at a temperature of 500°C. Then 100 grams of the aluminum oxide were impregnated with 44 ml of aqueous solutio of hexachloreplatinic acid (H$_2$PtCl$_6$), containing 38.2 mg of this acid per ml. The impregnated aluminum oxide was aged for half an hour at room temperature and then dried at a temperature of 120°C and heated in air for 1 hour at a temperature of 500°C. The catalyst thus prepared contained 0.8% by weight of platinum, 0.66% by weight of chloride, calculated as chloride, had a specific surface area of 185 m$^2$/gram and a pore volume of 0.44 ml/g and was formed into particles with maximum measurements between 0.177 and 0.420 mm. The bulk specific gravity was 0.66 g/ml.

Preparation of catalyst B

A very pure commercial aluminum oxide, different from the one used for the preparation of catalyst A, was heated in air for 1 hour at a temperature of 500°C. Then 100 g of the aluminum oxide were impregnated with 83 ml of an aqueous solution of hexachloroplatinic acid (H$_2$PtCl$_6$), containing 20.2 mg of this acid per ml. The impregnated aluminum oxide was aged for half an hour at room temperature, dried at a temperature of 120°C, and then heated in air for 1 hour at a temperature of 500°C. The catalyst thus prepared contained 0.8% by weight of platinum, 0.66% by weight of chloride, calculated as chlorine, had a specific surface of 230 m$^2$/g and a pore volume of 0.83 ml/g and was formed into particles having maximum measurements between 0.177 and 0.420 mm. The bulk specific gravity was 0.52 g/ml.

Hydrogenolysis

The catalysts A and B were tested in a fixed bed with a diameter of 1.2 cm. In both experiments a mixture consisting of 63.4 mol.% of ethylbenzene, 30.6 mol.% of 1-phenylethanol and 6.0 mol.% of methyl phenyl ketone with hydrogen in a molar ratio hydrogen: (1-phenylethanol + methyl phenyl ketone) of 1.45 was passed through the bed in a downward direction at a pressure of 12 bar abs. and a temperature of 350°C. The space velocity was 8 1/1/hour, which for catalyst A was 12.1 1/kg/hour and for catalyst B 15.4 1/kg/hour. Table C shows the results obtained after 5 hours of operation.

Table C

| Catalyst | conversion (1-phenyl-ethanol + methyl phenyl ketone | composition reaction product, mol% | | | compounds with a boiling point below 125°C |
|---|---|---|---|---|---|
| | | ethyl-benzene | ethyl cyclo-hexane | styrene | |
| A | 95 | 99.7 | 0.05 | 0.2 | 0.05 |
| B | 98 | 99.6 | 0.1 | 0.1 | 0.15 |

ILLUSTRATIVE EMBODIMENT IV

The catalysts A and B were again prepared in the same way as described in Illustrative Embodiment III, but now the catalysts were formed into cylindrical particles with a diameter of 1.5 and 5.5 mm respectively. The cylindrical particles of catalyst B and a cylindrically shaped hollow space the central axis of which coincided with that of the cylindrical particle; the diameter of the hollow space was 2.5 mm. These two catalysts and two fresh amounts of the catalyst A and B with the dimensions as mentioned in Illustrative Embodiment III were tested in a fixed bed by passing a mixture consisting of 63.4 mol.% of ethylbenzene, 30.6 mol.% of 1-phenylethanol and 6.0 mol.% of methyl phenyl ketone together with hydrogen in a molar ratio hydrogen (1-phenylethanol + methyl phenyl ketone) of 1.45 through the bed in downward direction at a pressure of 12 bar abs. and a temperature of 350°C. Within a period of 25 hours the space velocity was graudally reduced from 66.8 to 6 l/kg/hour. Table D shows the conversions of 1-phenylethanol and of methyl pehnyl ketone together. A dash indicates that the conversion has not been determined.

Table D

| | conversion %, catalyst | | | |
|---|---|---|---|---|
| | A, particle size in mm | | B, particle size in mm | |
| Space velocity | largest dimensions between 0.177 and 0.420 | diameter 1.5 | largest dimensions between 0.177 and 0.420 | diameter 5.5 |
| 66.8 | — | 81 | 89 | 91 |
| 32 | — | 92 | 95.5 | 97 |
| 25.8 | 93 | — | — | — |
| 16 | — | 97 | 99 | 99 |
| 12 | 95 | — | — | — |
| 8 | — | — | 100 | — |
| 6 | 100 | — | 100 | — |

ILLUSTRATIVE EMBODIMENT V

Catalysts with 0.8%, 0.4% and 0.2% by weight of platinum on the same aluminum oxide as in catalyst A of Illustrative Embodiment III and prepared in an analogous way were tested by passing starting mixtures of the same composition as in Illustrative Embodiment III through a fixed bed of each of the catalysts with a space velocity of 16 l/kg/hour at a temperature of 350°C. The beds consisted of cylinder shaped particles with a diameter of 1.5 mm. The remaining reaction conditions were as in Illustrative Embodiment III. Table E shows the conversions and compositions of the reaction product measured after 3 hours of operation.

Table E

| | conversion, % | | | composition reaction product, mol.% | | | |
|---|---|---|---|---|---|---|---|
| Cat. % by wt Pt | methyl phenyl ketone | 1-phenyl-ethanol | total | ethyl-benzene | ethyl-cyclo-hexane | styrene | compounds with a boiling point below 125°C |
| 0.8 | 88.4 | 99.5 | 97.6 | 99.1 | 0.1 | 0.4 | 0.4 |
| 0.4 | 85.1 | 99.0 | 96.9 | 98.9 | 0.1 | 0.7 | 0.3 |
| 0.2 | 73.6 | 98.7 | 94.6 | 99.0 | 0.05 | 0.7 | 0.3 |

ILLUSTRATIVE EMBODIMENT VI

Two fresh amounts of the catalyst B mentioned in Illustrative Embodiment III were tested, as described in Illustrative Embodiment III, at a temperature of 350°C and a space velocity of 4 l/kg/hour with the use of different molar ratios of hydrogen: (1-phenylethanol + methyl phenyl ketone). Table F shows the results at a time when the space velocity was momentarily raised from 4 to 16 l/kg/hour. The conversion of 1-phenylethanol always always greater than 99.5%.

Table F

| Hours of operation of start of experiment | conversion methyl phenyl ketone, %, at molar ratio $H_2$: (1-phenylethanol + methyl phenyl ketone) of | |
|---|---|---|
| | 1.25 (pressure 12 bar) | 2.4 (pressure 14.5 bar) |
| 2 | 94 | 96 |

Table F-continued

| Hours of operation of start of experiment | conversion methyl phenyl ketone, %, at molar ratio $H_2$: (1-phenylethanol + methyl phenyl ketone) of | |
|---|---|---|
| | 1.25 (pressure 12 bar) | 2.4 (pressure 14.5 bar) |
| 20 | 90 | 95 |
| 43 | 81 | — |
| 67 | 77 | — |
| 95 | — | 91 |
| 121 | 68 | — |
| 142 | — | 89 |

ILLUSTRATIVE EMBODIMENT VII

A starting mixture with the composition mentioned in Illustrative Embodiment III was passed through a fixed bed of catalyst B as mentioned in Illustrative Embodiment III, together with hydrogen in a molar ratio hydrogen: (1-phenyl-ethanol + methyl phenyl ketone) of 2.4, at a pressure of 7.5 bar abs. and a temperature of 300°C with a space velocity of 4 l/kg/hour. Table G shows the conversions of methyl phenyl ketone that were observed after the number of hours of operation indicated. The 1-phenylethanol was always wholly converted.

Table G

| hours of operation | conversion of methyl phenyl ketone | hours of operation | conversion of methyl phenyl ketone |
|---|---|---|---|
| 3 | 97.4 | 95 | 75.2 |
| 6 | 96.3 | 103 | 77.6 |
| 72 | 75 | 119 | 75.8 |
| 78 | 74.4 | | |

ILLUSTRATIVE EMBODIMENT VIII

Starting mixtures consisting of 83.3% by weight of ethylbenzene, 2.9% by weight of methyl phenyl ketone and 13.8% by weight of 1-phenylethanol were passed through fixed beds of the catalysts A and B together with hydrogen in a molar ratio hydrogen: (1-phenylethanol + methyl phenyl ketone) of 2.4 at a pressure of 14.5 bar abs. and a temperature of 350°C. The catalysts were commercial platforming catalysts consisting of pellets with a diameter of 1.5 mm containing 0.37 and 0.8% by weight of platinum respectively and 0.88% by weight and 0.44% by weight of chlorine respectively on aluminum oxide. Catalyst B also contained 0.44% by weight of fluorine. Table H shows the space velocities applied as well as the conversions and compositions of the reaction product observed.

Table H

| | | conversion, % | | composition reaction product, mol. % | | | |
|---|---|---|---|---|---|---|---|
| Cat. | space velocity l/kg/hour | methyl phenyl ketone | 1-phenyl-ethanol | ethyl-benzene | ethyl-cyclo-hexane | styrene | compounds with a boiling point below 125° |
| A | 14.5 | 97 | 100 | 99.5 | 0.3 | 0.05 | 0.1 |

Table H-continued

| Cat. | space velocity l/kg/hour | conversion, % methyl phenyl ketone | 1-phenyl-ethanol | composition reaction product, mol. % ethyl-benzene | ethyl-cyclo-hexane | styrene | compounds with a boiling point below 125° |
|---|---|---|---|---|---|---|---|
| B | 25.5 | 95 | 100 | 99.3 | 0.5 | 0.1 | 0.1 |

ILLUSTRATIVE EMBODIMENT IX

A starting mixture having the same composition as that in Illustrative Embodiment VIII was passed through a fixed bed of catalyst A mentioned in Illustrative Embodiment VIII at a temperature of 350°C. The pressure, the molar ratio hydrogen: (1-phenylethanol + methyl phenyl ketone) and the space velocity were varied as indicated in Table I. Table I also shows the conversions of methyl phenyl ketone that were observed after the number of hours of operation indicated. At the moment of observation the space velocity was raised to the values mentioned between brackets for a short period. After the hydrogenolysis of 1177 kg (methyl phenyl ketone + 1-phenylethanol) per kg of catalyst, air with a temperature of 400°C was passed through the catalyst bed. As a result of this the activity of the catalyst was completely recovered as is shown by the last three experiments mentioned in Table I.

Table I

| Pressure, bars | molar ratio $H_2$: (1-phenyl-ethanol + methyl phenyl ketone) | space velocity l/kg/hour | kg (methyl phenyl ketone and 1-phenyl-ethanol) per kg catalyst | conversion methyl phenyl ketone % |
|---|---|---|---|---|
| 14.5 | 2.4 | 1.66(14.6) | 15 | 99 |
|  |  |  | 60 | 97 |
|  |  |  | 184 | 87 |
|  |  |  | 235 |  |
| 29 | 2.4 | 3.32(29.2) | 378 | 70 |
|  |  |  | 480 | 66.5 |
|  |  |  | 550 | 65 |
| 1.5 | 2.4 | 1.66(14.6) | 604 | 71 |
|  |  |  | 731 | 60 |
|  |  |  | 778 | 53 |
| 29 | 6.0 | 2.3(12.2) | 800 | 88 |
|  |  |  | 967 | 85 |
|  |  |  | 1177 | 82.5 |
| 14.5 | 2.4 | 1.66(14.6) | 13 | 96 |
| 29 | 6.0 | 2.3(12.2) | 25 | 99 |
|  |  |  | 114 | 98.5 |

The 1-phenylethanol was always completely converted. Before the regeneration the reaction mixture continuously contained more than 98.8 mol% of ethylbenzene. After the regeneration the reaction mixture contained more than 99.5 mol% of ethylbenzene.

After 800 kg (methyl phenyl ketone + 1-phenylethanol) per kg of catalyst had passed the catalyst bed, the methyl phenyl ketone was still entirely converted at a space velocity of 2.3 l/kg/hour and the reaction mixture contained 3-4 mol.% of ethylcyclohexane. As a result of the short increase of the space velocity to 12.2 l/kg/hour, the conversion of the methyl phenyl ketone dropped to 88% (see table I) and the reaction product contained only 0.6-0.8 mol% of ethylcyclohexane.

After the regeneration the methyl phenyl ketone was wholly converted at a space velocity of 2.3 l/kg/hour and the reaction mixture contained 16.5 mol% of ethyl-cyclohexane. As a result of the short increase of the space velocity to 12.2 l/kg/hour the conversion of methyl phenyl ketone was 99% and the reaction product contained only 7 mol.% of ethylcyclohexane.

The content of ethylcyclohexane is 18 mol.% in case of thermodynamic equilibrium.

I claim as my invention:

1. A process for the preparation of alkyl benzenes by contacting phenyl alkyl ketones and/or phenyl alkanols in which alkanols the alkanol moiety has at least two carbon atoms and the phenyl and hydroxyl groups are attached to the same carbon atom, with hydrogen at a temperature between about 175°C and about 450°C and with a supported noble metal of Group VIII of the Periodic Table of the Elements as a catalyst.

2. The process of claim 1 wherein the temperature is maintained at a value between about 250°C and about 375°C.

3. The process in claim 1 wherein the starting material is contacted with the catalyst at a pressure between about 2 bars and about 40 bar abs.

4. The process in claim 1 wherein an aluminium oxide is used as carrier.

5. The process in claim 1 wherein the noble metal is used in a percentage by weight between about 0.01 and about 1.5 based in the carrier.

6. The process in claim 5 wherein the noble metal is used in a percentage by weight between about 0.3 and about 1 based on the carrier.

7. The process in claim 5 wherein platinum is used as the noble metal.

8. The process in claim 1 wherein methyl phenyl ketone is used as the phenyl ketone and/or 1-phenylethanol as the phenyl alcohol.

* * * * *